United States Patent [19]

Masuzawa et al.

[11] Patent Number: 4,942,245
[45] Date of Patent: Jul. 17, 1990

[54] BENZIMIDAZOLE DERIVATIVES

[75] Inventors: Kuniyoshi Masuzawa, Matsudo; Kyuya Okamura, Ohmiya; Keigo Nishino, Ohmiya; Mitsuo Ohashi, Ohmiya; Katsuya Awano, Oyama, all of Japan

[73] Assignee: Kyorin Pharmaceutical Co., Ltd., Tokyo, Japan

[21] Appl. No.: 180,065

[22] Filed: Apr. 11, 1988

[30] Foreign Application Priority Data

Apr. 20, 1987 [JP] Japan .................. 62-96818

[51] Int. Cl.$^5$ .................. C07D 235/28; C07D 235/30
[52] U.S. Cl. .................. 548/329; 548/325; 548/330; 548/333
[58] Field of Search ............. 548/329, 330, 333, 325

[56] References Cited

U.S. PATENT DOCUMENTS 4,440,935 4/1984 Huang .................. 548/306 X
4,680,398 7/1987 Irikura et al. .................. 548/329 X Primary Examiner—Richard A. Schwartz
Attorney, Agent, or Firm—Oblon, Spivak, McClelland, Maier, Neustadt

[57] ABSTRACT

Benzimidazole derivatives of the following formula,

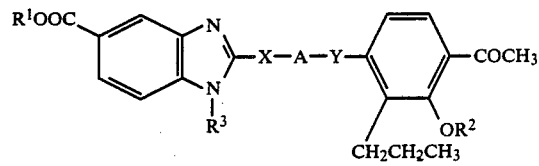

wherein $R^1$ indicates hydrogen atom, lower alkyl group having carbon atoms of 1 to 6 or dimethylaminopropyl group, $R^2$ indicates hydrogen atom or lower alkanoyl group having carbon atoms of 1 to 3, $R^3$ indicates hydrogen atom, lower alkyl group having carbon atoms of 1 to 3 or lower alkanoyl group having carbon atoms of 1 to 3, X indicates sulfur atom, sulfinyl group, sulfonyl group, amino group or methylene group, A indicates alkylene group having carbon atoms of 1 to 12, which alkylene group may optionally be substituted by hydroxy group or lower alkyl group having carbon atoms of 1 to 3, —(CHR')N—CR''=CR''—(CHR')M—,

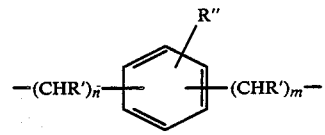

(in which R' and R'' are each independently hydrogen atom, lower alkyl group having carbon atoms of 1 to 3 or hydroxy group, and n and m are equal to 0, 1, 2 or 3) and Y indicates oxygen atom or sulfur atom; their acid or alkali salts and hydrate thereof are useful as antiallergic agents.

22 Claims, No Drawings

BENZIMIDAZOLE DERIVATIVES

DETAILED DESCRIPTION OF THE INVENTION

This invention is concerned with certain novel benzimidazole derivatives, which have strong and selective anti-leukotriene action and useful for prevention or treatment of allergic diseases such as asthma, their intermediates and process for their preparation thereof.

Moreover, it relates to certain novel benzimidazole derivatives of the formula (I),

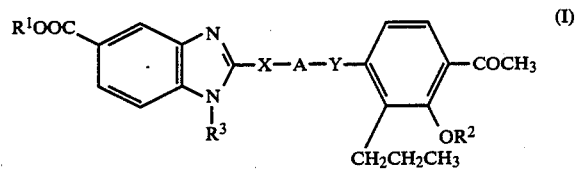

wherein $R^1$ indicates hydrogen atom, lower alkyl group having carbon atoms of 1 to 6 or dimethylaminopropyl group, $R^2$ indicates hydrogen atom or lower alkanoyl group having carbon atoms of 1 to 3, $R^3$ indicates hydrogen atom, lower alkyl group having carbon atoms of 1 to 3 or lower alkanoyl group having carbon atoms of 1 to 3, X indicates sulfur atom, sulfinyl group, sulfonyl group, amino group or methylene group, A indicates alkylene group having carbon atoms of 1 to 12, which alkylene group may optionally be substituted by hydroxy group or lower alkyl group having carbon atoms of 1 to 3, $-(CHR')_n-CR''=CR''-(CHR')_m-$,

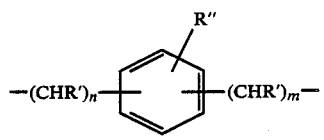

(in which R' and R'' are each independently hydrogen atom, lower alkyl group having carbon atoms of 1 to 3 or hydroxy group, and n and m are equal to 0, 1, 2 or 3), and Y indicates oxygen atom or sulfur atom; their acid or alkali salts and hydrate thereof.

Leukotrienes (leukotriene C4, D4 and E4), which are metabolites of arachidonic acid through 5-lipoxygenase pathway, are constituents of SRS-A (slow reacting substance of anaphylaxis), important mediator of the immediate type allergic disease such as bronchial asthma. For this reason, the drugs which antagonize leukotrienes are promising in treatment of bronchial asthma. But, the drugs having those effects through the internal use are unknown.

In a previous patent, the present inventors report having found that compounds represented by a general formula (described below) have a strong inhibitory action on leukotrienes-induced bronchoconstriction (Japan Kokai Pat. No. 61-186368 corresponding to European Pat. application No. 0 121 806).

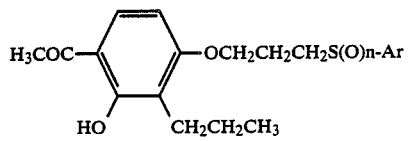

As a result of diligent studies, the inventors have found that compounds represented by a general formula (I) have a strong and selective inhibitory action on leukotriene-induced bronchoconstriction.

A benzimidazole derivatives represented by the following general formula (I),

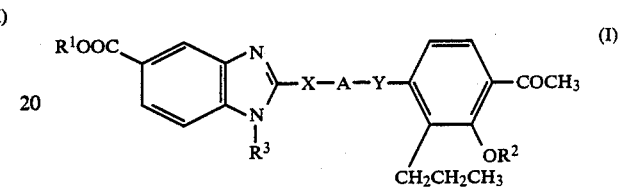

wherein $R^1$ indicates hydrogen atom, lower alkyl group having carbon atoms of 1 to 6 or dimethylaminopropyl group. $R^2$ indicates hydrogen atom or lower alkanoyl group having carbon atoms of 1 to 3, $R^3$ indicates hydrogen atom, lower alkyl group having carbon atoms of 1 to 3 or lower alkanoyl group having carbon atoms of 1 to 3, X indicates sulfur atom, sulfinyl group, sulfonyl group, amino group or methylene group, A indicates alkylene group having carbon atoms of 1 to 12, which alkylene group may optionally be substituted by hydroxy group or lower alkyl group having carbon atoms of 1 to 3, $-(CHR')_n-CR''=CR''-(CHR')_m-$,

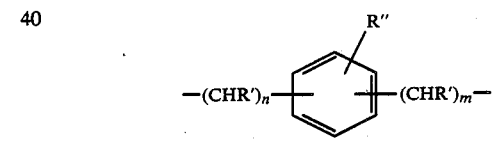

(in which R' and R'' are each independently hydrogen atom, lower alkyl group having carbon atoms of 1 to 3 or hydroxy group, and n and m are equal to 0, 1, 2 or 3), and Y indicates oxygen atom or sulfur atom, their acid or alkali salts and hydrate thereof.

According to the invention, the compounds represented by the general formula (I) are prepared by the following routes.

(1) The compounds wherein X is sulfur atom and $R^1$ is hydrogen atom in the general formula (I) can be prepared by allowing phenoxyalkyl derivatives represented by a general formula (III) or (III') to react with compounds of a general formula (II). Typically, they can be prepared by allowing phenoxy-alkyl derivatives (III) to react with compounds of the general formula (II) in suitable solvents such as, for example, dimethylformamide, dimethyl sulfoxide, alcohol and so on, in the presence of bases such as, for example, potassium carbonate, sodium carbonate, potassium hydroxide and so on.

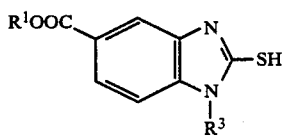

wherein R¹ and R³ are same as described above.

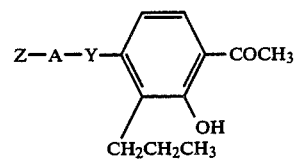

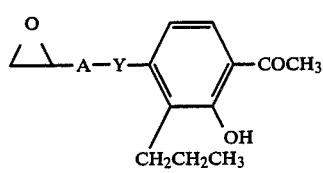

Wherein A and Y are same as described above and Z indicates a leaving group.

(2) The compounds wherein X is methylene group in the general formula (I) can also be prepared by allowing phenoxyalkyl derivatives represented by a general formula (V) to react with compounds of a general formula (IV). Typically, they can be prepared by allowing phenoxyalkyl derivatives (V) to react with compound of the general formula (IV) in suitable solvents such as, for example, methanol, ethanol and so on and then heated with alkali solution such as, for example, potassium hydroxide, sodium hydroxide and so on, under stirring.

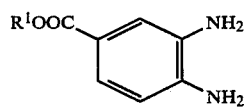

wherein R¹ is same as described above.

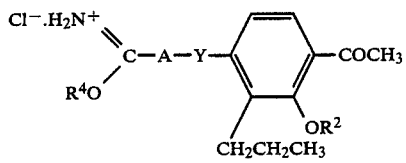

wherein R², A and Y are same as described above, R⁴ indicates lower alkyl group having carbon atoms 1 to 6.

(3) The compounds wherein X is sulfinyl group in the general formula (I) can be prepared by oxidizing compounds wherein X is sulfur atom in the general formula (I). Typically, they can be prepared by allowing compounds wherein X is sulfur atom in the general formula (I) to react with equivalent or excess amount of mild oxidizing agents such as, for example, m-chloroperbenzoic acid, hydrogen peroxide and so on, in suitable solvents such as, for example, dichloromethane, alcohol and so on.

(4) The compounds wherein X is sulfonyl group in the general formula (I) can be prepared by oxidizing compounds wherein X is sulfur atom in the general formula (I). Typically, they can be prepared by allowing compounds wherein X is sulfur atom in the general formula (I) to react with mild oxidizing agents similar to (3) in twice or more excess amounts.

(5) The compounds wherein R² is lower alkanoyl group in the general formula (I) can be prepared by esterification compounds wherein R² is hydrogen atom in the general formula (I) to react with acyl agent, for example. acyl halide or acid anhydride in inert solvents, for example, dichloromethane or chloroform in the presence of excess bases, for example. pyridine, triethylamine or 4-dimethylaminopyridine, or in pyridine only.

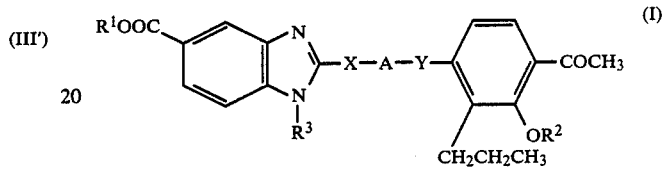

wherein R¹, R², R³, X, A and Y are same as described above.

Moreover, the compounds represented by the general formula (I) can be converted to the salts by treatment with acid or alkali. The acid may be inorganic acid such as, for example, hydrogen chloride, sulfuric acid, phosphoric acid and so on, or organic acid such as, for example, methanesulfonic acid, lactic acid, acetic acid, citric acid, tartaric acid and so on. The alkali may be alkali metal such as, for example, sodium, potassium and so on.

The compounds represented by the general formula (V) are new compounds and can be prepared from the compounds represented by the general formula (VI). Typically, they can be prepared by allowing hydrogen chloride to react with compounds of the general formula (VI) and alcohol in suitable solvents such as, for example, ether and so on, under stirring.

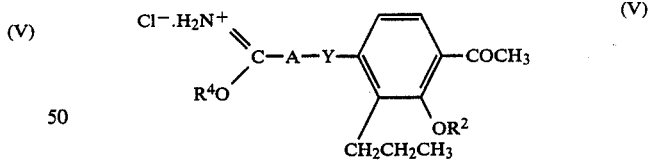

wherein R², R⁴, A and Y are same as described above.

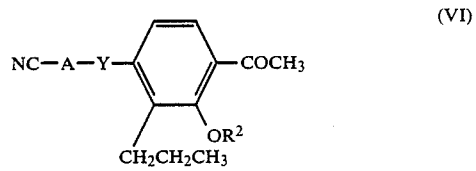

wherein R², A and Y are same as described above.

In following, the invention will be illustrated based on concrete examples, but the invention is not confined to these examples.

EXAMPLE 1

2-[3-(4-Acetyl-3-hydroxy-2-propylphenoxy)propyl-thio]benzimidazole-5-carboxylic acid A mixture of 2-mercaptobenzimidazole-5-carboxylic acid (3.25 g), 3-(4-acetyl-3-hydroxy-2-propylphenoxy)-propylbromide (2.00 g) and potassium hydroxide (1.27 g) in ethanol (30 ml) was refluxed for 4 hours. Then, the reacting mixture was poured into ice-water, made acidic with concentrated hydrochloric acid and extracted with ethyl acetate. The organic layer was dried over anhydrous sodium sulfate and then evaporated. The resulting residue was purified by silica gel column chromatography, eluting with dichloromethane-ethyl acetate-methanol (10:2:1), and recrystallized from n-hexane-ethyl acetate to give the title compounds (3.00 g, 67.1%) as pale yellow crystals, mp 106–108° C.

Analysis (%) for $C_{22}H_{24}N_2O_5S$: Calcd. (Found); C, 61.67 (61.76); H, 5.65 (5.89); N, 6.54 (6.26).

EXAMPLE 2

2-[2-(4-acetyl-3-hydroxy-2-propylphenoxy)ethylthio]-benzimidazole-5-carboxylic acid A mixture of 2-(4-acetyl-3-hydroxy-2-propylphenoxy)ethyl bromide (2.71 g), ethyl 2 mercaptobenzimidazole-5-carboxylate (2.00 g) and anhydrous potassium carbonate (1.49 g) in N,N-dimethylformamide (30 ml) was stirred at 80–90° C. for 30 minutes. The reaction mixture was poured into ice-water, made acidic with concentrated hydrochloric acid and extracted with ethyl acetate. The organic layer was washed with water, dried over anhydrous sodium sulfate and evaporated. The resulting residue was purified by silica gel column chromatography, eluting with dichloromethane-ethyl acetate (10:1), to give ethyl 2-[2-(4-acetyl-3-hydroxy-2-propylphenoxy)ethylthio]benzimidazole-5-carboxylate (2.33 g, 58.5 %) as a yellow oil.

The above ester (2.20 g) was added to 1 N sodium hydroxide solution (20 ml), and the mixture was refluxed for 30 minutes, then poured into ice-water, made acidic with concentrated hydrochloric acid and extracted with ethyl acetate. The organic layer was washed with water, dried over anhydrous sodium sulfate and evaporated. The resulting residue was purified by silica gel column chromatography, eluting with dichloromethane-methanol (10:1), and recrystallized from n-hexane-ethyl acetate to give the title compound (1.60 g, 77.1 %) as colorless crystals, mp 108–110° C.

Analysis (%) for $C_{21}H_{22}N_2O_5S$: Calcd. (Found); C, 60.86 (60.65); H, 5.35 (5.35); N, 6.76 (6.61).

EXAMPLE 3

2-[3-(4-Acetyl-3-hydroxy-2-propylphenoxy)-2-hydroxypropylthio]benzimidazole-5-carboxylic acid Ethyl 2-[3-(4-acetyl-3-hydroxy-2-propylphenoxy)-2-hydroxypropylthio]benzimidazole-5-carboxylate was prepared in a similar manner to Example 2 with 3-(4-acetyl-3-hydroxy-2-propylphenoxy)-1,2-epoxypropane (1.91 g) and ethyl 2-mercaptobenzimidazole-5-carboxylate (1.70 g). 2.10 g (58.1%) of the esters was obtained as a yellow oil. This ester (2.10 g) was converted to the title compound (870 mg. 44.1%) as pale brown crystals in the same manner as Example 2, mp 133–135° C.

Analysis (%) for $C_{22}H_{24}N_2O_6S$: Calcd. (Found); C, 59.45 (59.94); H, 5.44 (5.60); N, 6.30 (6.23).

EXAMPLE 4

2-[3-(3-Acetoxy-4-acetyl-2-propylphenoxy)propyl-thio]benzimidazole-5-carboxylic acid A mixture of 2-[3-(4-acetyl-3-hydroxy-2-propylphenoxy)-propylthio]benzimidazole-5-carboxylic acid (1.50 g), triethylamine (4 ml), acetic anhydride (4 ml) and 4-dimethylaminopyridine (100 mg) in dichloromethane (50 ml) was stirred at 0° C. and then at room temperature for 5 hours. Methanol (4 ml) was added to the mixture, further stirred for an additional 30 minutes and then the mixture was evaporated. The residue was washed with water, dissolved in ethanol, and concentrated to dryness. The residue was purified by silica gel column chromatography, eluting with dichloromethane-ethyl acetate-methanol (10:2:1), and recrystallized from n-hexane-chloroform to give the title compound (970 mg, 58.2%) as yellow crystals, mp 85–87° C.

Analysis (%) for $C_{24}H_{26}N_2O_6S \cdot \frac{1}{3} H_2O$: Calcd. (Found); C, 60.49 (60.64); H, 5.64 (5.78); N, 5.88 (5.72).

EXAMPLE 5

2-[3-(4-Acetyl-3-hydroxy-2-propylphenoxy)propylsulfinyl]benzimidazole-5-carboxylic acid To a mixture of 2-[3-(4-acetyl-3-hydroxy-2-propylphenoxy)-propylthio]benzimidazole-5-carboxylic acid (1.00 g) in dichloromethane (30 ml) and methanol (3 ml) stirring in ice-salt-water bath, was added m-chloroperbenzoic acid (80%, 503 mg) in a small portions below 0° C. Further stirring for an additional 15 minutes, the mixture was evaporated, and the residue was purified by silica gel chromatography, eluting with dichloromethane-ethyl acetate-methanol (10:2:1), and recrystallized from ethanol-water to give the title compound (540 mg, 52.1%) as colorless crystals, mp 173–175° C.

Analysis (%) for $C_{22}H_{24}N_2O_6S$: Calcd (Found); C, 59.45 (59.61); H, 5.44 (5.46); N. 6.30 (6.30).

EXAMPLE 6

2-[3-(4-Acetyl-3-hydroxy-2-propylphenoxy)propylsulfonyl]benzimidazole-5-carboxylic acid To a mixture of 2-[3-(4-acetyl-3-hydroxy-2-propylphenoxy)-propylthio]benzimidazole-5-carboxylic acid (1.08 g) in dichloromethane (30 ml) and methanol (3 ml), stirring at 5–10° C., was added m-chloroperbenzoic acid (80 %, 1.20 g) in a small portions. Further stirring for an additional 15 minutes, the mixture was evaporated. The resulting residue was purified by silica gel column chromatography, eluting with dichloromethane-ethyl acetate-methanol (10:2:1), and recrystallized from ethanol-water to give the title compound (890 mg, 76.7 %) as colorless crystals, mp 212–215° C. (decompd.).

Analysis (%) for $C_{22}H_{24}N_2O_7S$ Calcd. (Found); C, 57.38 (57.50); H, 5.25 (5.27); N, 6.08 (6.09).

EXAMPLES 7-31

Other new compounds (Examples 7-31) which were prepared by the same procedure as in Examples 1-6 are listed in Table 1.

TABLE 1

$R^1OOC$-benzimidazole-$S(O)_{n2}$-A-O-phenyl(-$COCH_3$)(-$OR^2$)(-$CH_2CH_2CH_3$)

| Example | A | $n_2$ | $R^1$ | $R^2$ | mp (°C.) | Yield (%) | Analysis Calcd. (%) Found C | H | N |
|---|---|---|---|---|---|---|---|---|---|
| 7 | —CH(CH$_3$)CH$_2$CH$_2$— | 0 | —CH$_2$CH$_3$ | H | oily | 77.3 | | | |
| 8*1 | —CH(CH$_3$)CH$_2$CH$_2$— | 0 | H | H | 106–108 | 40.4 | 60.78 60.56 | 6.06 5.78 | 6.16 6.17 |
| 9 | —(CH$_2$)$_4$— | 0 | —CH$_2$CH$_3$ | H | oily | 35.8 | | | |
| 10 | —(CH$_2$)$_4$— | 0 | —CH$_3$ | H | oily | 91.0 | | | |
| 11a | —(CH$_2$)$_4$— | 0 | H | H | 93–95 | 60.9 | 62.43 62.42 | 5.92 5.96 | 6.33 6.14 |
| 11b*2 | —(CH$_2$)$_4$— | 0 | H | H | 137–140 | 71.5 | 59.99 59.86 | 6.13 5.80 | 6.08 6.03 |
| 11c*3 | —(CH$_2$)$_4$— | 0 | H | H | 170–180 | 91.0 | 56.61 56.43 | 5.78 5.97 | 5.74 5.78 |
| 11d*4 | —(CH$_2$)$_4$— | 0 | H | H | 257–265 | 89.5 | 59.01 58.97 | 5.47 5.52 | 5.98 5.98 |
| 12 | —(CH$_2$)$_4$— | 1 | H | H | 93–95 | 73.4 | 60.25 60.15 | 5.72 5.63 | 6.11 5.86 |
| 13*5 | —(CH$_2$)$_4$— | 2 | H | H | 216–218 | 42.2 | 57.49 57.54 | 5.59 5.41 | 5.83 5.89 |
| 14 | —(CH$_2$)$_4$— | 0 | H | —COCH$_3$ | 85–87 | 72.8 | 61.97 62.03 | 5.82 5.86 | 5.78 5.58 |
| 15 | —(CH$_2$)$_4$— | 0 | —CH$_2$CH(CH$_3$)$_2$ | H | oily | 87.9 | 65.04 64.86 | 6.87 6.83 | 5.62 5.50 |
| 16 | —(CH$_2$)$_4$— | 0 | —CH$_2$CH(CH$_3$)$_2$ | —COCH$_3$ | oily | 97.9 | 64.42 64.17 | 6.71 6.67 | 5.18 5.06 |
| 17*6 | —(CH$_2$)$_4$— | 0 | —(CH$_2$)$_3$N(CH$_3$)$_2$ | H | 90–92 | 44.6 | 54.31 54.33 | 5.84 5.94 | 5.94 6.03 |
| 18 | —CH$_2$CH(OH)CH$_2$CH$_2$— | 0 | —CH$_2$CH(CH$_3$)$_2$ | H | oily | 75 | | | |
| 19 | —CH$_2$CH(OH)CH$_2$CH$_2$— | 0 | H | H | 116–117 | 31.8 | 60.25 60.09 | 5.72 5.83 | 6.11 6.49 |
| 20a*7 | —CH$_2$CH=CHCH$_2$— | 0 | —CH$_2$CH$_3$ | H | oily | 88.2 | | | |
| 20b*8 | —CH$_2$CH=CHCH$_2$— | 0 | —CH$_2$CH$_3$ | H | oily | 78.7 | | | |
| 21a*7 | —CH$_2$CH=CHCH$_2$— | 0 | H | H | 90–92 | 51.2 | 62.71 62.99 | 5.49 5.60 | 6.36 6.24 |
| 21b*8 | —CH$_2$CH=CHCH$_2$— | 0 | H | H | 93–95 | 31.0 | 62.71 62.64 | 5.49 5.60 | 6.36 6.06 |
| 22 | —CH$_2$—C$_6$H$_4$—CH$_2$— | 0 | —CH$_2$CH(CH$_3$)$_2$ | H | — | 80.2 | | | |
| 23 | —CH$_2$—C$_6$H$_4$—CH$_2$— | 0 | H | H | 220–221 | 70.7 | 66.10 65.70 | 5.34 5.32 | 5.71 5.62 |
| 24 | —(CH$_2$)$_5$— | 0 | H | H | 70–72 | 38.6 | 63.14 63.40 | 6.18 6.26 | 6.14 6.01 |
| 25 | —(CH$_2$)$_6$— | 0 | —CH$_2$CH$_3$ | H | oily | 89.8 | | | |
| 26*9 | —(CH$_2$)$_6$— | 0 | H | H | 165–175 | 52.4 | 59.22 59.33 | 6.16 6.21 | 5.52 5.54 |
| 27 | —CH(CH$_3$)CH$_2$CH$_2$CH$_2$— | 0 | —CH$_2$CH$_3$ | H | oily | 87.1 | | | |

TABLE 1-continued

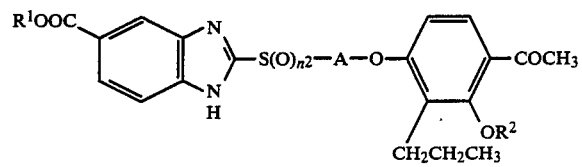

| Example | A | $n_2$ | $R^1$ | $R^2$ | mp (°C.) | Yield (%) | Analysis Calcd. (%) Found C | H | N |
|---|---|---|---|---|---|---|---|---|---|
| 28*10 | —CH(CH₃)CH₂CH₂CH₂— | 0 | H | H | 83–85 | 35.9 | 60.28 / 60.14 | 6.41 / 6.03 | 5.86 / 5.93 |
| 29 | —(CH₂)₈— | 0 | H | H | 72–75 | 40.3 | 65.04 / 65.18 | 6.87 / 6.90 | 5.62 / 5.54 |
| 30 | —(CH₂)₁₀— | 0 | —CH₂CH₃ | H | oily | 88.1 | | | |
| 31*1 | —(CH₂)₁₀— | 0 | H | H | 70–72 | 72.7 | 64.65 / 64.62 | 7.36 / 7.09 | 5.20 / 5.39 |

*1 ⅓H₂O,
*2 1H₂O,
*3 1HCl.½H₂O,
*4 1Na.1/5H₂O,
*5 ⅓H₂O,
*6 ½oxalate,
*7 E form,
*8 Z form,
*9 1HCl,
*10 6/5H₂O

EXAMPLE 32

5-(4-Acetyl-3-hydroxy-2-propylphenoxy)pentanimidate hydrochloride

Into a mixture of 5-(4-acetyl-3-hydroxy-2-propylphenoxy)-valeronitrile (5.5 g) and ethanol (0.95 ml) in ether (30 ml). cooled on ice-salt-water bath, was bubbled hydrogen chloride for 20 minutes below 0 ° C. The resulting solution was allowed to stand for 30 minutes at the same temperature and for overnight in a refrigerator. The mixture was evaporated under a reduced pressure and the resulting residue was triturated with anhydrous ether to give the title compound (4.0 g, 81.1%) as colorless crystals, mp 104–105 ° C.

Analysis (%) for $C_{18}H_{27}NO_4$ HCl.½ H₂O: Calcd. (Found); C, 58.93 (58.75); H, 7.97 (7.75); N, 3.82 (4.02).

EXAMPLE 33–35

Other new compounds (Examples 33–35) prepared by the same procedure as in Example 32 are listed in Table 2.

TABLE 2

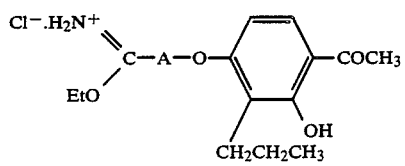

| Example | A | mp (°C.) | Yield (%) | Analysis Calcd. (%) Found C | H | N |
|---|---|---|---|---|---|---|
| 33 | —(CH₂)₃— | 95–97 | 91.2 | | | |
| 34* | —(CH₂)₅— | 103–105 | 88.7 | 60.99 / 61.02 | 8.15 / 8.06 | 3.74 / 3.85 |
| 35* | —(CH₂)₆— | 93–95 | 84.5 | 61.88 / 61.84 | 8.37 / 8.30 | 3.61 / 3.68 |

*½H₂O

EXAMPLE 36

2-[4-(4-Acetyl-3-hydroxy-2-propylphenoxy)butyl]-benzimidazole-5-carboxylic acid

A mixture of ethyl 5-(4-acetyl-3-hydroxy-2-propylphenoxy)-pentanimidate hydrochloride (3.0 g) and ethyl 3,4-diaminobenzoate (1.4 g) in ethanol (40 ml) was stirred at room temperature for 24 hours. To the mixture was added a solution of sodium hydroxide (1.6 g/30 ml of water) and the resulting mixture was refluxed for 40 minutes. After removal of the solvent under reduced pressure, the mixture was poured into ice-water, acidified with concentrated hydrochloric acid and extracted with ethyl acetate. The organic layer was washed with water and dried over anhydrous sodium sulfate. The extract was evaporated and the resulting residue was purified by silica gel column chromatography, eluting with dichloromethane-ethanol (9:1), to give the title compound (2.0 g, 58.1 %) as amorphous powder, mp 98–100 ° C.

Analysis (%) for $C_{23}H_{26}N_2O_5$ Calcd. (Found); C, 67.30 (67.14); H, 6.38 (6.40); N, 6.82 (6.85). Examples 37–39

Other new compounds (Examples 37–39) prepared by the same procedure as in Example 36 are listed in Table 3.

TABLE 3

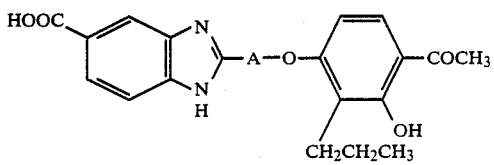

| Example | A | mp (°C.) | Yield (%) | Analysis Calcd. (%) Found C | H | N |
|---|---|---|---|---|---|---|
| 37 | —(CH₂)₃— | 216–219 | 60.7 | 66.65 / 66.41 | 6.10 / 6.09 | 7.07 / 7.00 |

TABLE 3-continued

Structure:
HOOC-benzimidazole(NH)-2-A-O-phenyl with COCH₃, OH, CH₂CH₂CH₃ substituents

| Example | A | mp (°C.) | Yield (%) | Analysis Calcd. (%) Found | | |
|---|---|---|---|---|---|---|
| | | | | C | H | N |
| 38 | —(CH₂)₅— | 99–102 | 27.8 | 67.91 | 6.65 | 6.60 |
| | | | | 67.90 | 6.64 | 6.54 |
| 39 | —(CH₂)₆— | 87–89 | 33.5 | 68.47 | 6.90 | 6.39 |
| | | | | 68.19 | 6.93 | 6.29 |

EXAMPLE 40

2-[4-(4-Acetyl-3-hydroxy-2-propylphenylthio)butylthio]benzimidazole-5-carboxylic acid (a) 4-(4-Acetyl-3-hydroxy-2-propylphenylthio)butylbromide To a refluxing mixture of 1.4-dibromobutane (32.9 g), anhydrous potassium carbonate (5.25 g) and potassium iodide (1 g) in acetone (100 ml) was added dropwise a solution of 2'-hydroxy-4'-mercapto-3'-propylacetophenone (8.00 g) in acetone (20 ml) during an hour and refluxed for 2 hours. The mixture was filtered off and the solvent was evaporated. The resulting residue was purified by silica gel column chromatography, eluting with benzene, to give the title compound (6.90 g, 52.6 %) as yellow oil.

(b) Ethyl 2-[4-(4-acetyl-3-hydroxy-2-propylphenylthio)butylthio]-benzimidazole-5-carboxylate A mixture of ethyl 2-mercaptobenzimidazole-5-carboxylate (1.29 g), anhydrous potassium carbonate (960 mg) in N,N-dimethylformamide (20 ml) was stirred at 60–70 ° C. for 30 minutes. To this mixture was added a solution of 4-(4-acetyl-3-hydroxy-2-propylphenylthio)butylbromide (2.00 g) in N,N-dimethylformamide (10 ml) dropwise during 10 minutes and stirred at the same temperature for 30 minutes. The reaction mixture was poured into ice-water, made acidic with concentrated hydrochloric acid and extracted with ethyl acetate. The organic layer was washed with water, dried over anhydrous sodium sulfate and evaporated. The resulting residue was purified by silica gel column chromatography, eluting with dichloromethane-ethyl acetate 10:1), to give the title compound (2.53 g, 89.8%) as pale yellow oil.

(c) 2 [4-(4-Acetyl-3-hydroxy-2-propylphenylthio)butylthio]benzimidazole-5-carboxylic acid A mixture of ethyl 2-[4-(4-acetyl-3-hydroxy-2-propylphenylthio)butylthio]benzimidazole-5-carboxylate (2.50 g), 1,4-dioxane (30 ml) and sodium hydroxide (1.03 g) in water (30 ml) was stirred at 60 ° C. for 2 hours. This mixture was poured into ice-water, made acidic with concentrated hydrochloric acid and extracted with ethyl acetate. The organic layer was washed with water, dried over anhydrous sodium sulfate and evaporated. The resulting residue was purified by silica gel column chromatography, eluting with dichloromethane-methanol (10:1), to give the title compound (1.52 g, 64.5 %) as yellow crystals, mp 90–95° C.

Analysis (%) for $C_{23}H_{26}N_2O_4S_2$: Calcd. (Found); C, 60.24 (60.01); H, 5.71 (5.86); N, 6.11 (5.93).

The compounds of this invention exhibit a powerful antagonizing effect on $LTD_4$ in the isolated guinea pig ileum. Furthermore, it is noteworthy that they exhibit remarkable effectiveness when administered orally.

A male Hartley guinea pig weighing about 450 g was anesthetized with sodium pentobarbital (30 mg/kg,i.p.). The change in transpulmonary pressure was measured by modifying the method of Konzett-Rössler (J. Harvey, et al., J. Pharmacol. Method. 9, 147–155, 1983) under an artificial ventilation. Animal was treated with indomethacin (10 mg/kg,i.v.) and propranolol (1 mg/kg,i.v.). Bronchoconstrictor response was obtained by bolus injection of leukotriene $D_4$ (3 μg/kg,i.v.). Test compounds were suspended in 5% Gum Arabic solution and orally administered 2 hours before the challenge with leukotriene $D_4$. As shown in Table 4, the compounds of the invention inhibited bronchoconstrictor response at lower oral doses than that of the reference compound.

TABLE 4

| Example | Dose (mg/kg,p.o.) | Inhibition (%) |
|---|---|---|
| 1 | 100 | 47.8 |
| | 200 | 63.3 |
| 6 | 200 | 40.5 |
| 11 | 25 | 27.6 |
| | 50 | 73.1 |
| | 100 | 84.6 |
| 12 | 200 | 33.3 |
| 24 | 200 | 57.1 |
| 36 | 100 | 44.6 |
| | 200 | 88.6 |
| Ref. 1* | 400 | 19.5 |

*2-[3-(4-acetyl-3-hydroxy-2-propylphenoxy)propylsulfonyl]-benzimidazole (Example 11 of Japan Patent Kokai 61-186368)

It is well-known that FPL55712, a typical leukotriene antagonist can exhibit no effect when administered orally (P. Sheard et al: Monogr. Allergy, P. 244–248, S. Karger, 1977).

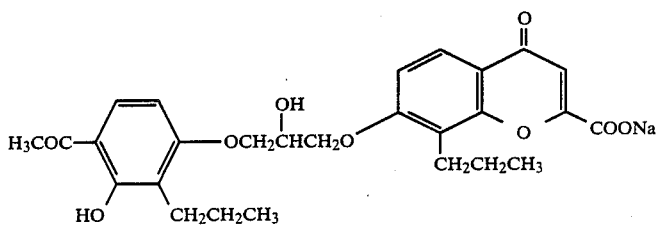

Sodium 7-[(3-(4-acetyl-3-hydroxy-2-propylphenoxy)-2-hydroxypropoxy]-4-oxo-8-propyl-4H-1-benzopyran-2-carboxylate Accordingly, the compounds of the invention are useful for the diseases in which leukotrienes play an important role, such as bronchial asthma, allergic rhinitis, allergic conjunctivitis, urticaria and so on.

What is claimed is:

1. A benzimidazole derivative of the formula (I):

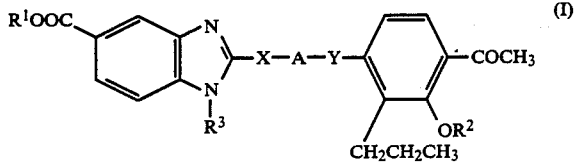

wherein:
- $R^1$ is a hydrogen atom, a $C_{1-6}$ alkyl group, or a dimethylaminopropyl group;
- $R^2$ is a hydrogen atom, or a $C_{1-3}$ alkanol group;
- $R^3$ is a hydrogen atom, $C_{1-3}$ alkyl group, or a $C_{1-3}$ alkanoyl group;
- X is a sulfur atom, a sulfinyl group, a sulfonyl group, an amino group, or a methylene group;
- A is an unsubstituted $C_{1-12}$ alkylene group, a $C_{1-12}$ alkylene group substituted by a hydroxy group or a $C_{1-3}$ lower alkyl group, a $-(CHR')_n-CR''=CR''-(CHR')_m-$ group, or a

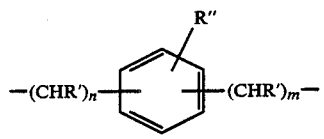

group, wherein R' and R'' are each independently a hydrogen atom, a $C_{1-3}$ alkyl group or a hydroxy group, and n and m are each independently equal to 0, 1, 2 or 3; and
- Y is an oxygen atom or a sulfur atom; or
- an acid or alkali salt or hydrate thereof.

2. The benzimidazole derivative of claim 1, wherein said acid salt of said compound of formula (I) is a hydrogen chloride salt, a sulfuric acid salt, a phosphoric acid salt, a methane sulfonic acid salt, a lactic acid salt, an acetic acid salt, a citric acid salt, or a tartaric acid salt.

3. The benzimidazole derivative of claim 1, wherein said alkali salt of the compound of formula (I) is an alkali metal salt.

4. The benzimidazole derivative of claim 1, wherein $R^1$ is a hydrogen atom.

5. The benzimidazole derivative of claim 1, wherein $R^1$ is a $C_{1-6}$ alkyl group.

6. The benzimidazole derivative of claim 1, wherein $R^1$ is a dimethylaminopropyl group.

7. The benzimidazole derivative of claim 1, wherein $R^2$ is a hydrogen atom.

8. The benzimidazole derivative of claim 1, wherein $R^2$ is a $C_{1-3}$ alkanoyl group.

9. The benzimidazole derivative of claim 1, wherein $R^3$ is a hydrogen atom.

10. The benzimidazole derivative of claim 1, wherein $R^3$ is a $C_{1-3}$ alkyl group.

11. The benzimidazole derivative of claim 1, wherein $R^3$ is a $C_{1-3}$ alkanoyl group.

12. The benzimidazole derivative of claim 1, wherein X is a sulfur atom.

13. The benzimidazole derivative of claim 1, wherein X is a sulfinyl group.

14. The benzimidazole derivative of claim 1, wherein X is a sulfonyl group.

15. The benzimidazole derivative of claim 1, wherein X is an amino group.

16. The benzimidazole derivative of claim 1, wherein X is a methylene group.

17. The benzimidazole derivative of claim 1, wherein A is an unsubstituted $C_{1-12}$ alkylene group.

18. The benzimidazole derivative of claim 1, wherein A is a $C_{1-12}$ alkylene group substituted by a hydroxyl group or a $C_{1-3}$ alkyl group.

19. The benzimidazole derivative of claim 1, wherein A is a $-(CHR')_n-CR''=CR''-(CHR')_m-$ group.

20. The benzimidazole derivative of claim 1, wherein A is a

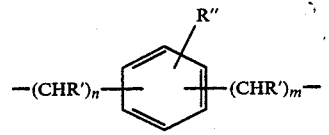

group.

21. The benzimidazole derivative of claim 1, wherein Y is an oxygen atom.

22. The benzimidaole derivative of claim 1, wherein Y is a sulfur atom.

* * * * *